United States Patent [19]

Lehmer

[11] Patent Number: 4,983,901
[45] Date of Patent: Jan. 8, 1991

[54] DIGITAL ELECTRONIC FOOT CONTROL FOR MEDICAL APPARATUS AND THE LIKE

[75] Inventor: Donald E. Lehmer, Berkeley, Calif.

[73] Assignee: Allergan, Inc., Irvine, Calif.

[21] Appl. No.: 342,254

[22] Filed: Apr. 21, 1989

[51] Int. Cl.$^5$ .............................................. G05B 19/40
[52] U.S. Cl. ........................................ 318/685; 604/65
[58] Field of Search ......................... 318/685; 604/65;
112/262.1; 128/752; 364/413.09

[56] References Cited

U.S. PATENT DOCUMENTS

| 4,526,114 | 7/1985 | Martell et al. | 112/262.1 |
| 4,758,220 | 7/1988 | Sundblom et al. | 604/65 |

Primary Examiner—William M. Shoop, Jr.
Assistant Examiner—Saul M. Bergmann
Attorney, Agent, or Firm—Howard R. Lambert

[57] ABSTRACT

A digitial electronic foot pedal control system, especially for medical apparatus and the like having a plurality of operating functions which can be selected among, comprises a pivotally mounted pedal shaft and a foot-operated pedal fixed to the shaft to pivot therewith. Included are a shaft encoder connected to the shaft for producing a digital shaft position output signal indicative of pedal shaft position relative to a reference position and a plurality of address cards each having N addresses corresponding to N given shaft positions. Each address card corresponds to one or more medical apparatus functions and is selected when a corresponding function or functions are selected, each of the addresses on each address card corresponding to a particular shaft rotational position and each storing a given set of control output signals for operating the corresponding function or functions. A counter counts the shaft position output signal from the encoder; address pointers derived from the count are applied to the appropriate address card to thereby cause the outputting therefrom of the appropriate sets of control signals as the foot pedal shaft is rotated. A stepper motor is connected for driving the shaft in a rotational direction toward the shaft reference position when the shaft is displaced therefrom and when the stepper motor is energized by an appropriate control signal, thereby providing a resistance to, but not preventing, further pedal rotational movement away from the reference position so as to provide tactile information regarding pedal position and possible changes in apparatus function.

25 Claims, 5 Drawing Sheets

DIGITAL ELECTRONIC FOOT CONTROL FOR MEDICAL APPARATUS AND THE LIKE

BACKGROUND OF THE INVENTION

1. Field of the Invention

The present invention relates generally to medical apparatus; more particularly, to operating controls for such apparatus; and, even more particularly, to foot-operated controls for medical apparatus and the like.

2. Background Discussion

Most powered medical apparatus include operating controls for setting and/or regulating parameters or functions of the apparatus. Such medical apparatus which require only an initial set up or only minor control adjustments during operation, usually locate all the controls in or on the apparatus cabinet, as opposed to remotely locating the controls, as is discussed below. Typical of such medical apparatus are simple X-ray machines, for which the operating parameters are usually preset by cabinet mounted controls before an X-ray is taken.

Numerous types of medical apparatus include, as part of the apparatus, a connected, hand-held medical implement or tool, some operating parameters or functions of which must usually be controlled during use. A familiar example of such medical apparatus are dentists' drilling apparatus which typically include a power source having connected thereto a hand-held drilling implement which requires drilling speed regulation and on/off control during its use on dental patients.

Another, perhaps less familiar, example of such medical apparatus are phacoemulsifier apparatus which are especially constructed for surgically removing the natural, crystalline lenses from cataract eyes in preparation for the insertion of an artificial intraocular lens. Phacoemulsifier apparatus typically comprise a cabinet, which contains a power supply, vacuum pump, electronic, and associated hardware, and a connected multi-function, hand-held surgical implement having a slender hollow needle-like tube which is inserted into a patients eye in order to perform the phacoemulsion operation. Functions of the phacoemulsifier hand-held surgical implement include irrigating the eye (with a saline solution), ultrasonically emulsifying (disintegrating) the eye lens, aspirating (by vacuum) the emulsified lens, cauterizing broken blood vessels, and vitrectomy (removing vitreous humor from the eye). It can be appreciated that a surgeon using the hand-held implement to perform such functions requires the ability to control these functions, as well as the ability to selectively shift or switch between at least some of the functions (for example, irrigation and irrigation plus aspiration) as the need arises during phacoemulsion surgery.

It can be appreciated that for such medical apparatus as dental drills and phacoemulsifiers, which require the use of hand-held implements for operations during which the operator requires functions of the implement to be shifted and/or varied, the complete controlling and/or shifting of functions from remote, cabinet-mounted controls is generally unsatisfactory. Normally, the person using the hand-held implement is too involved in the medical procedure to be able to operate remotely located, cabinet-mounted controls. On the other hand, having an attendant operate the cabinet-mounted controls is even less practical except, perhaps, for simple medical procedures and apparatus.

Such problems associated with adjusting cabinet-mounted controls while operating an associated hand-held medical implement may be overcome, in some simple cases, by mounting controls directly on the hand-held implement. This may, for example, be satisfactory when the only control required is to turn a function performed by the hand-held implement on and off and/or to vary an operational speed of a function performed by the implement. Then, the including on the implement of a ON/OFF microswitch perhaps with the additional inclusion of speed control, may be feasible for some medical apparatus (the implement then being analogous to a conventional, hand-held, variable-speed electric drill used by caprenters and homeowners). However, surgery performed by a skilled surgeon requires extremely precise control and, therefore, attempting to control a function with the same hand that is simultaneously manipulating the hand-held implement to perform a delicate operation is generally not preferred.

As an alternative (or a supplement) to cabinet-mounted and/or hand-held implement-mounted controls foot controls are frequently provided for medical (and other) apparatus, thereby freeing an operator's hands so that he or she can concentrate on manipulating the hand-held implement. Some such foot pedal controls, for example, have heretofore used one or more electrical switches mounted along the path of pedal movement so as to enable one or more operational functions to be respectively turned on and off by the operator depressing and releasing the foot pedal. In addition or alternatively, electric potentiometers have heretofore been connected to the pedal to enable the varying of an operational function by analog means according to the angle through which the pedal is displaced by the operator.

Mechanical detents are also known to have been used for providing increased resistance to angular pedal movement at preestablished detent points, thereby providing a sensory warning to the operator that slightly further pedal depressing will cause a given event to occur. For example, such detents may be used to alert the operator to the turning off of one operational function and the turning on of another function by a control switch or switches mounted in the path of pivotal pedal movement.

Heretofore, however, foot pedal controls for medical apparatus and the like have, so far as is known to the present inventor, been analog (as opposed to digital) types and have had, at least partly as a result, a number of deficiencies and disadvantages, some of which are serious. One disadvantage is that known analog foot pedal controls cannot be electronically "reprogrammed" to control different functions or combinations of functions, as is often important for use with multi-function apparatus, such as the above-described phacoemulsifiers. Another disadvantage is that when mechanical detents are used on analog foot pedal controls to alert the operator to an impending event, such as a switch being actuated, the detents tend to become worn with use and may eventually fail to provide sufficient additional resistance to pedal movement to give the desired warning to the operator. On the other hand, mechanical detents may become dirty and tend to stick, and may, therefore, result in excessive pedal pressure having to be applied to overcome the detent, thereby possibly resulting in greater-than-intended pedal travel and failure of proper foot pedal control once the pedal is moved past the detent position.

For these and other reasons, improvements in foot pedal control systems, particularly for use with medical apparatus, are needed; and it is a principal objective of the present invention to provide such an improved digital foot pedal control system which is particularly suited for controlling multi-function apparatus.

SUMMARY OF THE INVENTION

In accordance with the present invention, there is provided a digital electronic foot pedal control system, especially for medical apparatus and the like, which comprises a pedal mount, a pedal shaft pivotally connected to the mount, and a foot-operated pedal fixed to the shaft to pivot therewith. Non-rotatably connected to the pedal shaft are digital shaft rotational position indicating means which provides a digital shaft position output signal representative of pedal shaft angular position relative to a pedal zero reference position. Included in the pedal control system are logic means which comprise digital storage means for storing N given sets of output control signals corresponding to N given pedal shaft angular positions relative to the reference position, and processing means connection for receiving shaft position output signals from the shaft rotational position indicating means and, responsive thereto, for causing the outputting from the storage means of corresponding sets of control signals for operating the medical apparatus or the like, the sets of control signals being appropriate for the shaft rotational positions represented by the received shaft position output signals.

According to a preferred embodiment of the invention, the digital storage means include an address card having N address positions corresponding to the N given shaft rotational positions, and each such address position storing a preestablished set of control output signals which are appropriate for the associated pedal position. Also, the control system preferably includes counting means for counting the shaft position output signals from the shaft rotational position indicating means and for deriving therefrom appropriate address pointers for application to the address card. If the medical apparatus or the like to be controlled by the foot pedal control system has a plurality of operating functions and means for selecting among such functions or associated groups of such functions, the digital storage means include a plurality of address cards in parallel, each such card corresponding to one or more of the functions, an appropriate address card being selected in response to the selecting means selecting among the functions of the medical apparatus of the like.

Advantageously, the foot pedal control system may further include motor means, preferably comprising a stepper motor, connected to the pedal shaft so as to tend to drive the shaft in a rotational direction back toward the zero shaft reference position when the pedal is displaced therefrom and when the motor means are energized. The motor means thereby provides a resistance to, but does not prevent, further pedal rotational movement away from the zero reference position. In such case, the given sets of output control signals stored in the digital storage means include control signals for causing the energizing of the motor means at given pedal shaft rotational positions in accordance to the function or functions to be controlled by the foot pedal control system.

BRIEF DESCRIPTION OF THE DRAWINGS

The present invention may be more readily understood by a consideration of the following detailed description when taken in conjunction with the accompanying drawings, in which:

FIGS. 2a-c are electrical schematic drawings illustrating a preferred manner in which the food pedal control system of FIG. 1 can be implemented in digital electronics form; FIG 2a showing part of the electronics, FIG. 2b showing substantially the rest of the electronic circuitry, and FIG. 2c essentially showing a pin connection table. When the same features and elements are shown in more than one figure, the same reference numbers are used in each figure.

DESCRIPTION OF THE PREFERRED EMBODIMENT

Figure 1:
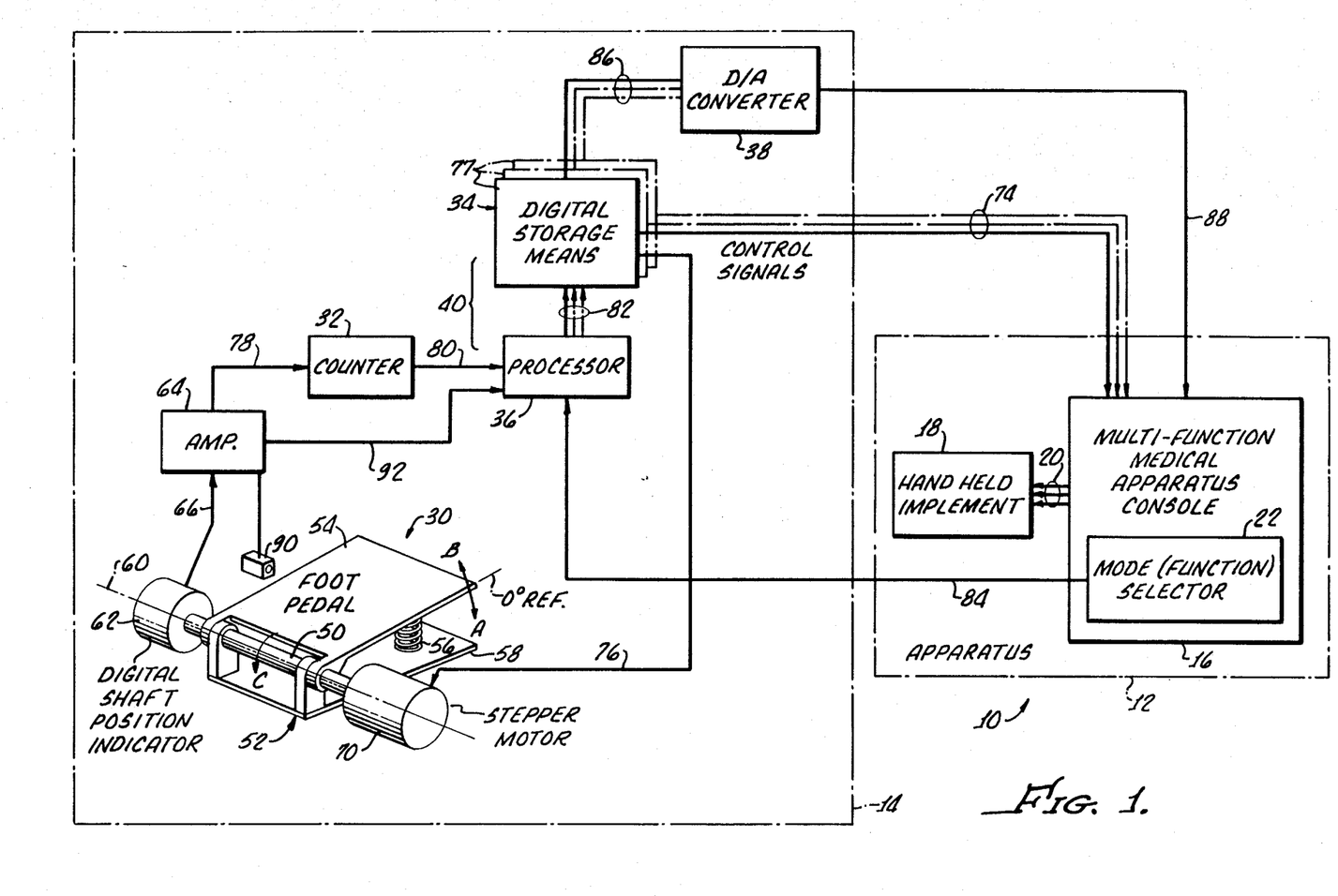
FIG. 1 is a drawing, partly in diagramatic form and partly in functional block diagram form, showing an electronic, digital foot pedal control system, in accordance with the present invention, and showing foot pedal and control and logic portions of the system.

There is depicted in FIG. 1 an exemplary medical equipment system 10 which comprises generally a medical apparatus 12 having operatively connected thereto a digital electronic foot control system 14 in accordance with the present invention. Medical apparatus 12 may, as depicted for illustrative and descriptive purposes and with no limitation thereto being either intended or implied, be of a multi-function medical phacoemulsifier. Forming medical apparatus 14 are an equipment console or cabinet 16 and an associated hand-held medical implement or tool 18 which is operably connected to the console by an umbilical 20 typically several feet in length.

Console 16 is preferably constructed for housing all of the equipment necessary for enabling the functioning of medical apparatus 12 in a prescribed manner through hand-held implement 18. For a phacoemulsifier, console 16 may, for example, include a power supply, a vacuum pump, a source of ultrasonic power, a fluid irrigation pump, a source of irrigating fluid, and various other hardware and electronic circuits, none of which are shown as they do not form any part of the present invention. Assuming that medical apparatus 14 is a multifunction apparatus, console 16 includes a manually-operated function or mode selector 22 by means of which the various operational functions or modes of operation are selected among. As mentioned above, the functions of a phacoemulsifier include irrigation, lens emulsification, irrigation and aspiration, cauterization, and vitrectomy.

Generally comprising foot pedal control system 14, to which the present invention is directed, and as is depicted in FIG. 1 and more particularly described below, are foot pedal means or assembly 30, a digital counter 32, digital storage means 34, data processor means 36, and digital to analog (D/A) converter 38. Together, digital storage means 34 and data processor means 36 can be considered to form a logic means 40.

Foot pedal assembly 30 comprises a pedal shaft 50 which is rotationally mounted in a pedal housing or mount 52, only part of which is shown in FIG. 1. Non-rotably fixed to central regions of pedal shaft 50 is a foot pedal 54 which is biased or urged, for example, by a spring or springs 56, to a zero rotational reference position (that is, the undepressed position). In operation, foot pedal 54 is depressed by an operator's foot downwardly (direction of arrow A) toward a housing base plate 58, spring 56, when foot pressure on pedal 54 is released, returning the pedal (in the direction of Arrow B) to the zero reference position.

Non-rotatably connected to one end region of pedal shaft 50, on a shaft rotational axis 60, is a bidirectional digital rotational position detector or shaft encoder 62, which may be of a known type. Shaft encoder 62 may be connected to pedal shaft 50 through a drive, for example, a 5:1 speed up drive (as described below). As pedal 54 is depressed from the zero reference position, digital position detector 62 provides a digital signal to an amplifier 64, over a conduit 66, the digital signal containing data relative to the rotational motion of pedal shaft 50 relative to the zero reference position. Detector 62 may, for example, be configured for providing a series of N outputs corresponding to N given angular positions of foot pedal.

Connected to the opposite end region of pedal shaft 50, also along shaft axis 60, are motor means 70, which preferably comprise a stepper motor of a known type. Motor means 70 are importantly connected for driving pedal shaft 50 in a counterclockwise or "return" direction direction (direction of Arrow C) when the motor means are energized (as described below) at one or more preselected (given) pedal angular positions relative to the zero reference position, according to the particular function or function to be performed by implement 18. At pedal rotational positions at which motor means 70 are energized, an operator is required to apply additional foot pressure on pedal 54 to overcome the driving torque on shaft 50 provided by motor means, the increased foot pressure required to depress foot pedal 54 serving to alert the operator that some preestablished or given event, such as the switching from one operational function to another, will occur if the foot pedal is depressed further. As is described below, motor means 70 can be programmed to be energized at any desired angular position of foot pedal 54, and the angular foot pedal positions at which motor means 70 is energized may be different for different functions to be controlled by foot pedal control system 14.

It is, of course, known beforehand what operations or sequence of operations are required to be performed by an operator using implement 18 to perform a surgical (or other) procedure. As an illustration, it is known that an ophthalmic surgeon performing phacoemulsion surgery ordinarily employs the following sequence of operations or functions: (i) irrigation of the eye with a saline solution, (ii) a combination of simultaneous irrigation and aspiration of the irrigating fluid, and (iii) a combination of fluid irrigation of the patient's eye, the ultrasonic emulsification of the eye lens, and the aspiration of the irrigation fluid and broken up particles of the lens. During this process, the surgeon may, however, want the option of switching back to just fluid irrigation and fluid aspiration without lens emulsification. These functions are referred to as modes, and are selected at the front panel of console 16 and are directed to foot pedal processor 40 by mode selector 22.

In any event, it is known beforehand what kind of control is required of foot pedal control system 14 in order to provide the functional operation of hand-held implement 18, for each of the possible modes. It is accordingly, required of logic means to provide the necessary functional control signals to console 16 (over a conduit or group of conduits 74) so that for example, at a certain predetermined (and convenient) angular position of foot pedal 54, a signal is provided by logic means 40 "directing" console 16 to provide a flow of irrigating fluid to implement 18, and at another predetermined, angular position of the foot pedal to provide emulsifying ultrasonic energy to the implement. It is, of course, to be understood that the control provided by foot pedal control system 14 to implement 18, through console 16, should be repeatable. That is, certain specific control signals should be provided by foot pedal control system 14 whenever foot pedal 54 is at a specific angular positions and the same sequence of signals should be provided at the same positions whenever the foot pedal is depressed.

The function of foot pedal shaft position indicator or encoder 62 and counter 32 is to precisely, accurately, and repeatably provide to logic means 40 digital output signals which correspond to and are representative of the angular position of foot pedal 54 relative to its zero (undepressed) position. Encoder 62 provides signals which are decoded by counter 32 into increment or decrement events. In this manner, counter 32 provides a numerical representation of the angular position of foot pedal 54, such representation being used by processor 40 as a pointer into digital storage means 34. Based upon "learning" from pedal shaft position indicator 62 the exact angular position of foot pedal 54, it is a function of logic means 40 to provide, to console 16, the requisite control signals associated with that foot pedal position.

Another function of logic means 40 is to provide energizing signals to motor means 70, over a conduit 76, whenever pedal shaft indicator means 62 signals the logic means that pedal 54 is at a predetermined angular position at which the energizing of motor means is required to provide pedal back pressure.

Accordingly, memory means 34 are configured for storing whatever predetermined sets of control signals are needed to be provided to console 16 as foot pedal 54 is depressed from its zero (at rest) position to its fully depressed position. Preferably, memory means 34 are configured for storing N sets of given control signals to be provided to console 16 for N corresponding angular positions of foot pedal 54 (that is, of pedal shaft 50) as detected or determined by position indicator 62 and counter 32. Generally among some of the N sets of given control signals stored in storage means 34 are one or more control signals causing the energizing of motor means 70 at given pedal shaft angular positions.

Memory means 34 may advantageously be in the form of an address card 77 having N addresses, and in which each address corresponds to a particular one of the N angular positions of foot pedal 54 (that is, of pedal shaft 50). In each of the N address positions of address card 77 there is stored the set of digital output control signals required for the corresponding pedal shaft position. Processor 36 functions to decode the signals from shaft angular position indicator 62 in conjunction with counter 34 provides a corresponding address "pointer" into address card 77. Thus, when foot pedal 54 is depressed by an operator, position indicator 62 provides a series of output signals which are counted by counter 32 to produce data related to the angles through which pedal shaft 50 is rotated. These output signal are provided, over a conduit 78, to counter 32, which, responsive thereto, provides digital counts, over a conduit 80, to processor 36. Responsive thereto, processor 36 provides a corresponding sequence of address "pointers," over a conduit 82, to memory means 34 (that is, to address card 77), each of the address pointers corresponding to a particular angular position of pedal shaft 50, as determined by position indicator 62. Whenever an address pointer is received by storage means 34, the set of control signals in the address "pointed " to is outputted, over conduit 74, to console 16, wherein the control signals are used to control functions of apparatus 12 in a given manner.

In addition to providing particular output control signals to console 16, storage means 34 preferably provide particular digital output signals (according to the accessed addresses in the storage means) over a conduit 86, to digital-to-analog (D/A) converter 38. A corresponding analog signal is provided from D/A converter 38, over a conduit 88, to console 16 for the operation of variable controls in apparatus 12, such as emulsification power which is responsive to an analog voltage signal.

A reset switch 90, preferably of the optical type, is mounted adjacent to foot pedal 54 and is connected to processor 36 and counter 32 (through amplifier 64), by a conduit 92, for resetting the processor when the foot pedal is at its zero position. This resets counter 32 when pedal 54 is at the zero position.

The use of a plurality of similar address cards 77 to comprise storage means 34 is advantageous, since each address card can be provided with N sets of given sets of output control signals (corresponding to N different addresses and N given foot pedal angular positions) appropriate for a particular function (or group of functions) which apparatus 12 is required to perform through hand-held implement 18. The appropriate address card 77 is selected, through processor 36, by function selector 22 on console 16 when a given function (or group of functions) of the apparatus is selected. For example, in the case of a phaco emulsifier, one function is irrigation only, another is irrigation and aspiration and emulsification, another is vitrectomy and still another is cautery. Once a particular function (or group of functions) is selected by selector 22, the corresponding address card 77 in storage means 34 is concurrently selected so that as address pointers are generated in processor 36 (as above-described), the address pointers are directed to the selected address card whose N sets of output control signals are appropriate for the selected function.

As a consequence, the selection of a particular address card 77 in storage means 34 in effect reprograms the control provided by foot pedal 54. That is, the full travel of foot pedal provides N particular sets of given out control signals to console 16 when one address card 77 is selected and another, different set of control signals to the console when another address card is selected, still another N sets of output control signals when still another address card is selected, and so on. This reprogramming of foot pedal 54 is depicted, by way of illustrative example, for a phacoemulsifier in the following Table, which shows the different operations enabled by the foot pedal as a function of foot pedal travel. Although it is shown in the Table that functions within operations switch at the same pedal positions for all the operations, it is to be understood that address cards 77 can be programmed such that there is, if desired, no such uniformity.

| Function | FOOT SWITCH POSITION | | | |
| --- | --- | --- | --- | --- |
|  | a | b | c | d |
| Irrigation/ Aspiration | no function | Irrigation | Irrigation/ Aspiration | Irrigation/ Aspiration |
| Phacoemulsion | no function | Irrigation | Irrigation Aspiration | Irrigation/ Aspiration/ Emulsification |
| Vitrectomy Wet Field | no function | Irrigation | Irrigation/ Aspiration/ Cutting | Irrigation/ Aspiration/ Cutting |
| Cautery (Voltage) | no function | Cautery | Cautery | Cautery |

For purposes of better illustrating the present invention relating to foot pedal control system 14, counter 32, digital storage means 34, processor 36, and D/A converter 38 are shown (FIG. 1) and are described above as being separate from one another and from apparatus 12, as may sometimes be advantageous. However, it is to be appreciated that such is not necessarily the case and that counter 32, storage means 34, processor 36, and/or D/A converter may alternatively be integrated together and/or may alternatively be fully integrated into apparatus 12, for example, into console 16. It is also to be appreciated that amplifier 64, although shown in FIG. 1 as being separate from foot pedal assembly 30, may advantageously be integrated thereinto so as to form a convenient, compact unit. The purpose of amplifier 64 is to enable conduits 78 and 92 to be of substantial length with the majority of components being remote from foot pedal assembly 30. Moreover, although conduits 76, 78, and 92 are depicted in FIG. 1 as being separate conduits, it will be appreciated that, in practice, such conduits would be bundled together in a single cable assembly connected to foot pedal assembly 30.

Figure 2A:
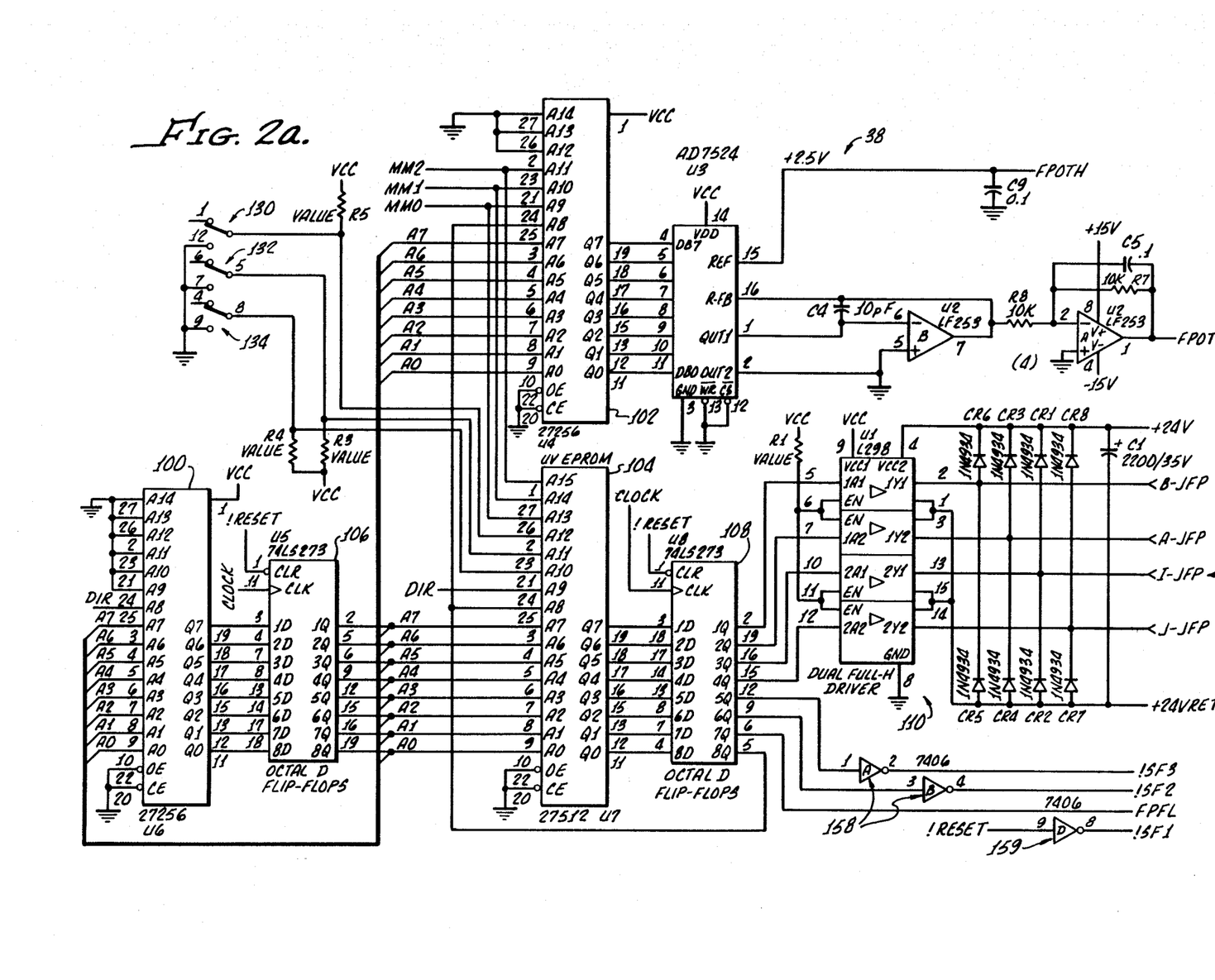
Figure 2B:
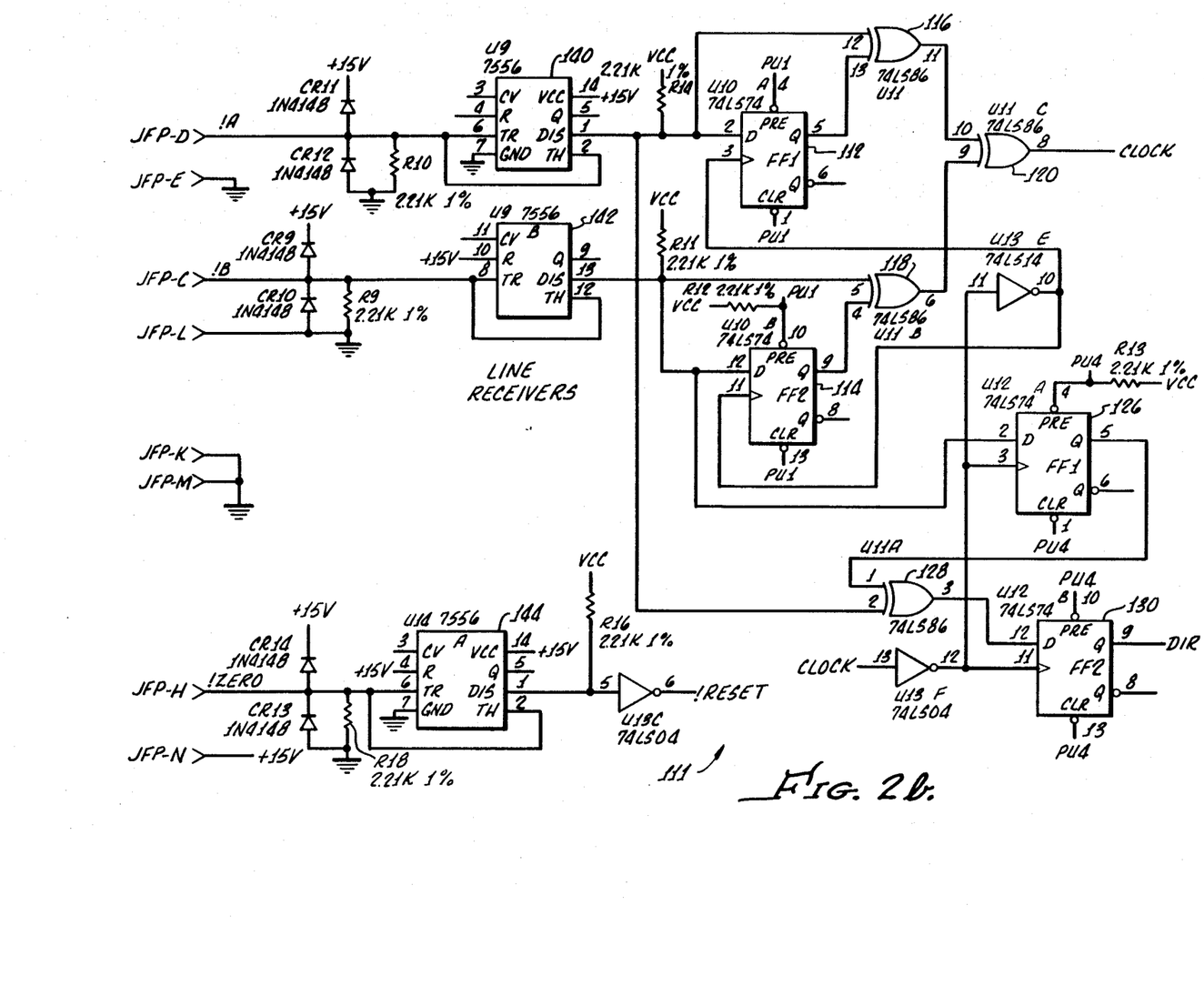
Figure 2C:
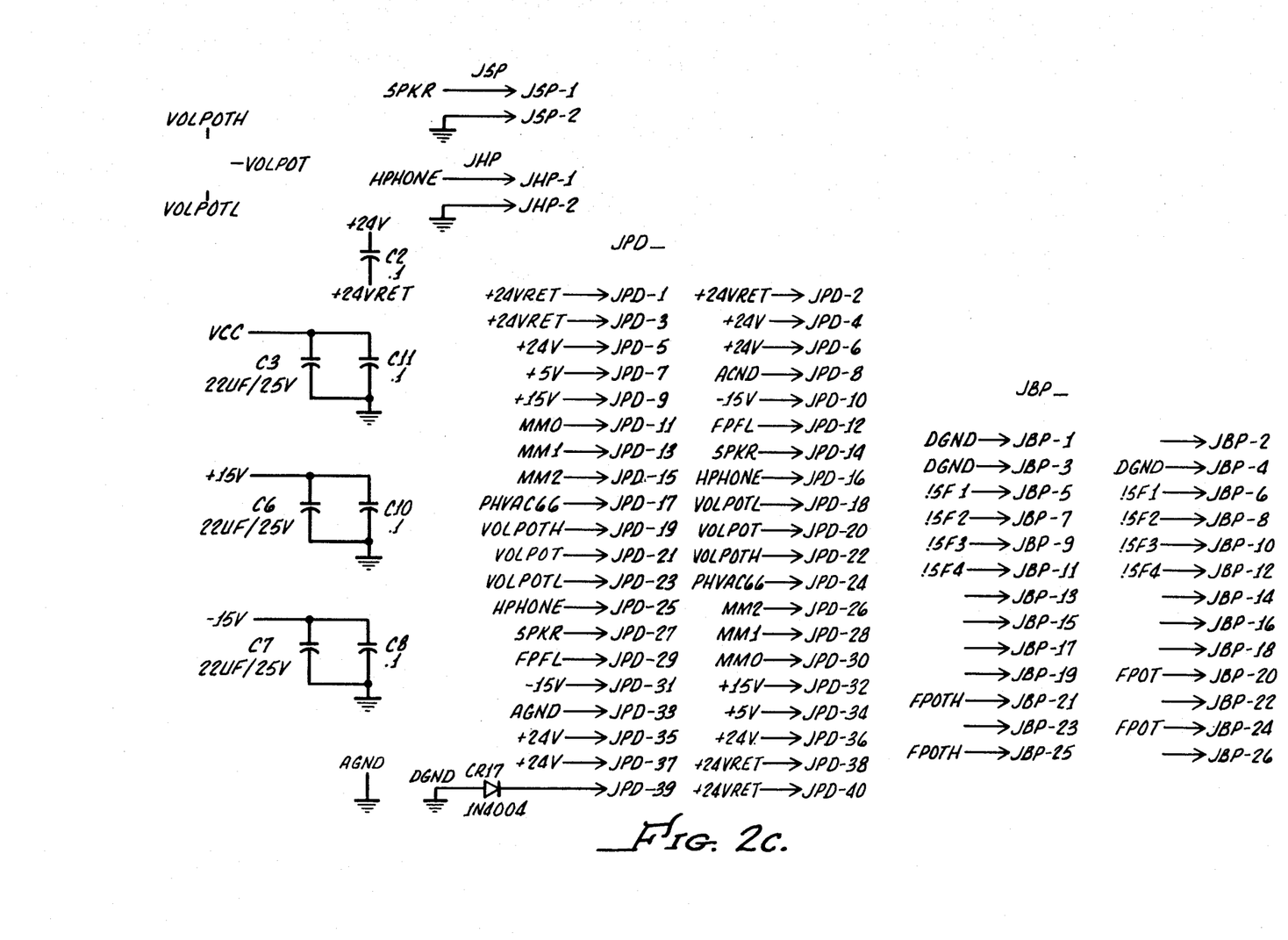

CIRCUITRY OF FIG. 2

It can be appreciated that foot pedal control system 14, as depicted in FIG. 1, and as is described above, can be electronically implemented in a number of ways. For example, the functions of counter 32, processor 36 and memory means 34 could be performed by a general purpose computer which is programmed in a manner know to those skilled in the programming arts. However, the present inventor has determined that the particular implementation shown in the electrical schematic of FIG. 2 is useful and offers various advantages such as relatively small size and the use of conventional solid state electronic components.

Moreover, it is considered that the electrical schematic of FIG. 2 is self-explanatory to those skilled in the electronics art and, in essence, provides a blueprint for the construction of above-described foot pedal control system 14, since all the components are labeled. For this reason, the present inventor considers it would be superfluous and excessively verbose to describe such circuit in detail. Nevertheless, a description of the principal features of the circuitry shown in FIG. 2 is presented hereinbelow, as are appropriate portions of an associated computer program.

Pedal position counter 32 determines the address pointers for three EPROMS 100, 102 and 104 which are addressed in parallel to form a 24 bit output. The EPROMs contain all the data for counter 32. D/A converter 38, the data for controlling the functions of apparatus 12 and stepping motor drive 110. Note that motor 70 is a stepping motor, requiring new data to be output as the motor turns to always create the desired upward torque.

The circuitry depicted in FIG. 2 consists generally of three EPROMs 100, 102, and 104; two data latches 106 and 108, D/A converter (DAC) 38; a motor driver 110 (all shown in FIG. 2a), and decoding logic 111 (all shown in FIG. 2b) for shaft encoder 62 (FIG. 1). The circuitry in FIG. 2b has two outputs, a clock pulse and a direction line which are decoded from the two shaft encoder 62 outputs which are in quadrature.

The two quadrature signals from shaft encoder 62 are presented to two D type latches 112 and 114 (FIG. 2b) and to one input of two exclusive OR gates 116 and 118. The other input of each such exclusive OR gates 116 and 118 is connected to the output of the corresponding latch 112 and 114. This circuit detects the difference between the present state of each latch 112 and 114 and its future state, the D input. If there is a difference, and there can only be a difference in one of the two since the signals cannot change at the same time the output of the corresponding exclusive OR gate 116 and 118 is true. Since only the one, can be true at a time, the next exclusive OR gate 120 output is true, thus this OR gate 120 functions as an OR gate.

The output of such OR gate 120 clocks both latches 112 and 114, eliminating the difference and resetting the clock pulse, which is inverted twice to add delay for adequate setup time for the latches. This produces a clock pulse for any change, producing four clock pulses for each encoder cycle.

Shaft encoder 62 has the resolution of one degree per cycle, yielding a resolution of 0.25 degree per clock pulse. The five to one speed up from pedal motor shaft 50 (FIG. 1) gives resolution of 0.05 degrees, thereby giving a resolution of 36 clocks per step since the stepping motor steps 1.8 degrees per step.

The determination of direction is done on the trailing edge of the clock pulse to allow for setup time. Here the two shaft encoder signals are compared to each other, one being delayed from the previous clock by a latch 126 (FIG. 2B) and the other being the current state. An exclusive OR gate 128 therefore determines the difference to indicate direction. A quadrature pattern is shown for shaft encoder signals A and B:

| Column | 1<br>A B | 2<br>A B | 3<br>A B |
|---|---|---|---|
|  | 0 0 | 0 0 | 0 0 |
|  | 0 1 | 0 1 | 0 1 |
|  | /<br>1 1 | 1 1 | 1 1 |
|  | /<br>1 0 | 1 0 | 1 0 |
|  | /<br>0 0 | 0 0 | 0 0 |

Note that only one bit changes at a time in A and B as pedal shaft 50 rotates

Note that only one bit changes at a time in A and B, as pedal shaft 50 rotates. Thus, if shaft 50 (FIG. 1) is turning such that the number sequence moves down the page, the previous state of A is always different from B, column 2, and that if the shaft is turning such that the number sequence moves up the page, the previous state of A is always the same as B, column 3.

Latch 130 is clocked on the trailing edge of the clock and maintains the direction data from exclusive OR gate 128 and is therefore an indication of shaft rotational direction. Latch 130 is the direction data for EPROMS 100 and 104. EPROM latches 106 and 108 store the data output of the EPROMs 100 and 104 used respectively for counting and data. The output of the some bits in latches 106 and 108 forms the address input to corresponding EPROMS 100 and 104, allowing a counter to be constructed. Latches 106 and 108 are reset by switch 90 (FIG. 1) at the top of the pedal travel to start the EPROM data from zero, and, therefore, the counter data from zero.

D/A converter 38 is connected to the data output of EPROM 102 and generates an analog output proportional to pedal position. The analog data output can start at any pedal position and have any span, as programmed by the EPROM.

EPROM 100, which is also referred to as the COUNTER EPROM, contains data which is separated into two pages, 256 bytes each, selected by the direction output of the shaft encoder decoder, the output of latch 130, signal name DIR. The data is latched into latch 106 by the clock output of gate 120 (FIG. 2b) and forms the next address of EPROM 100. The data in one page is one greater than the address and the data in the other page is one less than the address, forming the low order byte of a 512 state counter.

EPROM 104, which is also referred to as the DAC (D/A converter) EPROM, contains five or address cards 77, one for each of the phacoemulsifier modes. Each page represents an address card and contains data for EPROM 104, which generates the analog output of the pedal interface. The analog output can start at zero and change to a base voltage at any specified angle, and then increase to full scale at any angle. This type of operation is that which is desired by the application. Any data programmed into EPROM 102 could produce any analog output as desired.

EPROM 104, which is also referred to as the DATA EPROM, contains an additional counter bit to form a 512 state counter, the control data for the phacoemulsifier functions, the control data for stepper motor 70, and generates an over-run error caused, for example, by an error in counting. A specific mode and DIP selected control type, mentioned below, requires 1k of EPROM, 512 bytes for each encodore direction. Three DIP switches 130, 132 and 134 (FIG. 2a) allow the user to select one of eight possible 1k pages in any mode. These selections are made by DIP switches, 130, 132, and 134 which modify EPROM 104 addresses via inputs A10, A11, and A12. This allows each mode an 8K page, selected by the mode, via A13, A14, and A15 (FIG. 2a). Switch 134 changes the operation of the switch such that there are no motor control data when pedal is moving up since one half of each 1k page (used when the direction control indicates that pedal 54 is going up) contains no motor codes. This is not true for "Cautery" or "Mode Zero." (Mode Zero is a pedal check out mode of operation typically performed prior to surgical use of the apparatus.) This allows an operator to suppress detents when pedal 54 (FIG. 1) is released. This 2k page or card is then repeated four times, the page being selected by the four possible combinations of DIP switches 130 and 132 and each page being associated with a different type of stepping motor operation; no data, hence, off; motor on for one half step; motor on for one full step; and motor on for a full step followed by a half step. Each has a different tactile feedback to the operator.

Figure 3:
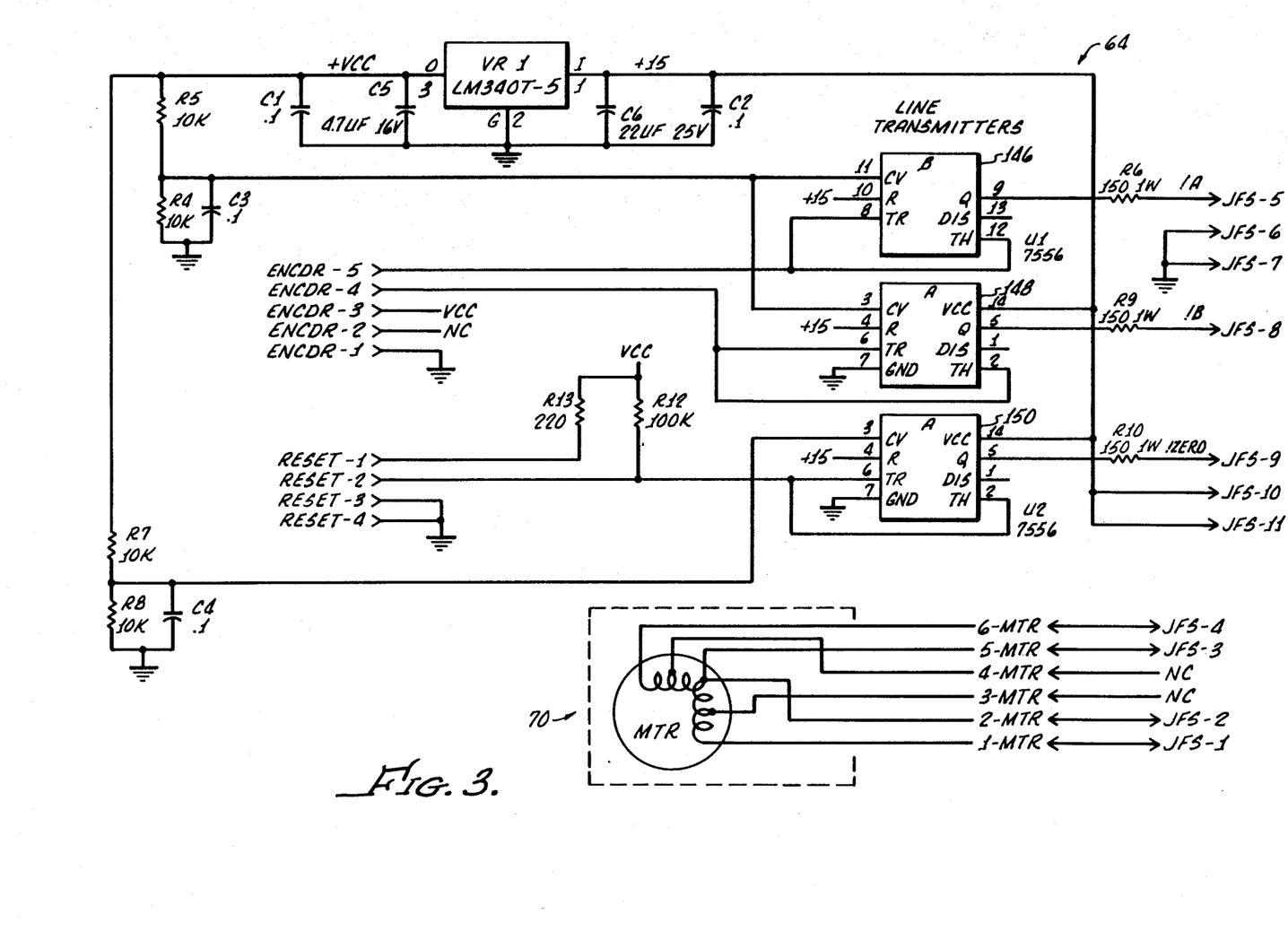
FIG. 3 is a schematic of electronic circuitry at the foot pedal end of the foot pedal control system.

As shown in FIG 2B, three line receivers 140, 142, and 144 are provided for receiving signals from the foot pedals circuitry shown in FIG. 3. Corresponding line transmitters 146, 148, AND 150 (FIGS. 3) are provided at the foot pedal end of system. (FIG. 2C merely provide pin connection information).

The PASCAL program that follows generates the following data files which must be assembled to form EPROMs 100, 102 and 104. The files are text of the form .BYTE XXX, where XXX is in decimal. These ASCII files must be assembled to form code files for EPROMs 100, 102, and 104. The following files are generated:

Counter EPROM: COUNT.TEXT Data > and < the address (.5k)
DAC EPROM (4k): ZERODAC.TEXT Diagnostic DAC data for Mode 0

| | |
|---|---|
| CAUTDAC.TEXT | DAC data for Cautery Mode |
| IRRDAC.TEXT | DAC data for I/A Mode |
| PHACODAC.TEXT | DAC Data for (phaco mode) |
| VITDAC.TEXT | DAC Data for Vitrectomy Mode |

Control EPROM: ZERO0.TEXT Diagnostic Mode, no feedback (2K)

| | | |
|---|---|---|
| ZERO1.TEXT | Diagnostic Mode, motor on | (6k) |
| CAUTO.TEXT | Cautery Mode, no feedback | (2k) |
| CAUT3.TEXT | Cautery Mode, motor on | (6k) |
| IRR0.TEXT | I/A MODE, no feedback | (2k) |
| IRR1.TEXT | I/A Mode, half step | (2k) |
| IRR2.TEXT | I/A Mode, full step | (2k) |
| IRR3.TEXT | I/A Mode, half and full step | (2k) |
| PHACOx.TEXT | Phaco Mode, as above | (8k) |
| VITx.TEXT | Vitrectomy Mode, as above | (8k) |

The Cautery mode has only one on/off position and turns on stepper motor 70 after the first level. Since motor 70 does not operate in plateaus, ZERO1.TEXT and CAUT3.TXT are repeated in place of the half and full step feedback modes.

| Angle | Counter | ZERO | CAUT | IRR | PHAC | VIT |
|---|---|---|---|---|---|---|
| 25.6 | 511 | FP3* | FP1* | FP2 | FP3 | FP2 |
| 25.2 | 504 | FP3* | FP1* FP2 | FP3 | FP2 | |
| 23.4 | 468 | FP3* | FP1* | FP2 | FP3 | FP2 |
| 21.6 | 432 | FP3* | FP1* | FP2 | FP3 | FP2 |
| 19.8 | 396 | FP3* | FP1* | FP2 | FP3 | FP2 |
| 18.0 | 360 | FP3* | FP1* | FP2 | FP3 | FP2 |
| 16.2 | 324 | FP3* | FP1* | FP2 | FP3 | FP2 |
| 14.4 | 288 | FP3* | FP1* | FP2 | FP3 | FP2 |
| 12.6 | 252 | FP3* | FP1* | FP2 | FP3 | FP2 |
| 10.8 | 216 | FP3* | FP1* | FP2 | FP3 | FP2 |
| 9.0 | 180 | FP2* | FP1* | FP2* | FP2 | FP2 |
| 7.2 | 144 | FP2* | FP1* | FP2 | FP2 | FP2 |
| 5.4 | 108 | FP2* | FP1* | FP2 | FP2 | FP2 |
| 3.6 | 072 | FP1* | FP1* | FP1* | FP1* | FP1* |
| 1.8 | 036 | FP1* | FP1* | FP1 | FP1 | FP1 |
| 0.0 | 000 | FP1* | FP1* | FP1 | FP1 | FP1 |

The following are the address assignments for EPROMs 100, 102 and 104

| | | | |
|---|---|---|---|
| 15 | | | M2 |
| 14 | | | M1 |
| 13 | | | M0 |
| 12 | | | S2 |
| 11 | | M2 | S1 |
| 10 | | M1 | S0 |
| 09 | | M0 | D |
| 08 | D | C8 | C8 |
| 07 | C7 | C7 | C7 |
| 06 | C6 | C6 | C6 |
| 05 | C5 | C5 | C5 |
| 04 | C4 | C4 | C4 |
| 03 | C3 | C3 | C3 |

| Address | Counter | DAC | Control |
|---------|---------|-----|---------|
| 02 | C2 | C2 | C2 |
| 01 | C1 | C1 | C1 |
| 00 | C0 | C0 | C0 | where C0–C8 are the address pointers from counter 32, D is encoder direction data, S0–S2 are the DIP switches 130, 132, and 134, and M0-M2 are the phacoemulsifier modes. From the address table it can be seen that the COUNTER EPROM 100 is separated into two 256 byte pages or cards based upon direction. The data is latched into latch 106 by the shaft encoder clock to form the next address, thereby forming the low order byte of the counter. DAC EPROM 102 is addressed by the 512 states of counter 32, and the phacoemulsifier modes. This allows digital to analog data to be selected based upon mode and pedal position. Direction is not included.

DATA EPROM 104 generates the high order bit of counter 32 in its first bit, expanding the counter to 512 states. This makes a minimum page 1k, 512 bytes per encoder direction. Note that different stepping motor control data can be included in EPROM 104 for different pedal pivotal directions since the EPROM is separated into two pages by the direction control bit. This allows the operation of pedal feedback to be excluded when pedal 54 goes up if desired. DIP switch 134 selects this option. The other two DIP switches 130 and 132 select half step and full step, with no feedback being neither, and the most feedback being both.

The phacoemulsifier modes form the top page selection such that any mode can have any control pattern The modes differ; Cautery has one on/off state followed by motor 70 being on, I/A and Victrectomy have one on/off state and one plateau followed by linear control, and Phaco has two on/off states and two plateaus followed by a linear portion. These differences are easily accommodated by this programmable design.

GENERATING PROGRAM

The PASCAL program includes the following procedures:

PROCEDURE SETUP

Generates 1024 bytes of data equal to the first motor control code (PHASE[0], followed by 1024 byte-of the next full step code, PHASE [2]. These are used to adjust reset switch 90 to achieve a uniform relationship between the pedal position and shaft position when pedal assembly 52 is initially assembled.

PROCEDURE COUNT

Generates data one greater and one less than the EPROM address in two 256 byte pages (512 bytes).

PROCEDURE CONVERT

Generates the data for the DAC based upon START, BASE and FULLSCALE. BASE is the voltage at the angle START and FULLSCALE is the angle where the DAC will be full scale. Generates five files, XXXXDAC.TEXT, where XXXX is the mode (512 bytes per mode).

PROCEDURE CONTROLD

Generates the high order counter bit, mode function data, an over-run error and stepping motor control. Case statements are used to set the angle where the data is to be generated. CONTROLD is for the angle going down, pedal going up. The selected angle is converted to stepping motor codes by using a table of codes for the eight half steps of the motor, PHASE. The motor codes are generated based upon the conditional ONUP, which generates the second page of data without the motor feedback when the pedal is released This procedure is called by CONTROLU, similar but for pedal 54 going down.

PROCEDURE CONTROLU

Similar to above, PROCEDURE CONTROLD, except for the pedal going down. The case statement numbers are one greater than the numbers in CONTROLD to cause a one digit dead band.

Stepper motor 70 is a 1.8 degree motor, 0.9 degree half step. The shaft encoder has a one degree cycle, or 0.25 degree per state (address change). Shaft encoder 62 is connected to the motor (that is, to the pedal shaft 50) via a 5:1 timing belt such that one state on the encoder is 0.05 degrees of the motor, or 18 states (addresses) per half step.

The expression PHASE [I DIV 18 MOD 8] points to one of eight half step motor codes which is proper to create the necessary torque for any address (I). This software array is used to place the proper codes for the motor driver into EPROM 104 based upon the angle.

The following is a simplified version of the PASCAL software to generate EPROMs 100, 102, 104. The output is ASCII files which contains the form .BYTE XXX, where XXX is decimal. This must be assembled to form a code file for EPROMs 100, 102, and 104. This is done such that the data generated would be transportable to other computer systems.

```
PROCEDURE SETUP;        (*Setup EPROM*)
BEGIN
    FOR I: = 0 TO 1023 DO
WRITELN(DEVICE,'-
.BYTE',PHASE[0]);
    FOR I: = 0 TO 1023 DO
WRITELN(DEVICE,'-
.BYTE',PHASE[2]);
END;
PROCEDURE COUNT:
    (*Count EPROM*)
BEGIN
```

```
    FOR I: = 1 TO 255 DO
WRITELN(DEVICE,'-
.BYTE',I:4);
    WRITELN(DEVICE,'-
.BYTE 0');
    WRITELN(DEVICE,'-
.BYTE 255');
    FOR I: = 0 TO 254 DO
WRITELN(DEVICE,'-
.BYTE', I:4);
END;
  (* Generates
COUNT.TEXT, two 256 byte
pages.
  The first page (up) ranging
[1.2.3.4. . .255.0]
  The second page (down)
ranging [255.0.1.2. . .254]
  The hardware depicted in
FIG. 2 latches this data to form
  the next address of the
EPROM 100 forming a
reversible
  counter.*)
PROCEDURE CONVERT;
(*DAC EPROM*)
BEGIN
      OUTPUT: = 0;
      SPAN1: =
FULLSCALE[MODE ] -
START [MODE];
      SPAN2: = 255 -
BASE[MODE];
FOR I: = 0 TO 511 DO
BEGIN
IF I > = START[MODE]
THEN
  OUTPUT: = ROUND
(((SPAN2/SPAN1)*(I-
START[MODE])) +
BASE[MODE]);
  IF OUTPUT > 255 THEN
OUTPUT: = 255;
  WRITELN(DEVICE,'-
.BYTE',OUTPUT:4);
END;
  (* Calculates slope
(SPAN1/SPAN2) and
multiplies same by the
  current angle, then adds the
base to form the DAC value.
  Over-travel holds the analog
value at full scale. This is
  called by the main program
for each mode and generates
  XXXDAC.TEXT.*)
PROCEDURE
CONTROLD;  (*DATA
EPROM 104 for pedal 54
going up*)
BEGIN
HOLD: = 0; MOTOR: =
FALSE;
  FOR I: = 0 to 511 DO
BEGIN
  IF I = 0 THEN CODE: =
1 ELSE CODE: = ((I-1) DIV
256);
CASE I OF 100:IF
MODES[MODE] <>
'CAUT' THEN HOLD: =
FP2;
  217:IF (MODES[MODE]
= 'PHACO') OR
(MODES[MODE] =
'ZERO')
THEN HOLD: = FP3;
END;
  IF MODES [MODE] =
'ZERO' AND ((HALF) OR
(FULL) THEN
```

-continued

```
  CASE I OF 1:MOTOR: =
TRUE;
END;
  IF (ONUP) AND
(MODES[MODE] <>
'ZERO')THEN
CASE I OF 54:IF FULL
THEN MOTOR: = TRUE;
  71:IF (FULL) AND (NOT
HALF) THEN MOTOR: =
FALSE;
  72:IF HALF THEN
MOTOR: = TRUE;
  89:IF MODES[MODE]
<> 'CAUT' THEN
MOTOR: = FALSE;
END;
  IF (ONUP) AND
(MODES[MODE ] =
'PHACO') THEN
CASE I OF 162:IF FULL
THEN MOTOR: = TRUE;
  178:IF (FULL) AND (NOT
HALF) THEN MOTOR: =
FALSE;
  180:IF HALF THEN
MOTOR: = TRUE;
  196:MOTOR: = FALSE;
END;
  IF MOTOR THEN CODE:
= CODE + PHASE[I DIV
18 MOD 8] * 16;
CODE: = CODE + HOLD;
IF I > MAXANGLE THEN
CODE: 1 + OVER;
IF I > 508 THEN CODE: =
1);
WRITELN(DEVICE,'-
BYTE',CODE:4); END;
WRITELN(DEVICE); END;
  (*Generates a 512 byte file
which contains a high order
  counter bit, two bits for foot
pedal level, (FP2/FP3), an
  over-run bit (OVER), and
four bits of stepper motor
driver
  data. These codes are stored
in the table PHASE, eight
  codes, one for each half step.
CONTROLD (ABOVE) is
called
  by CONTROLU (below) *)
PROCEDURE CONTROLU;
(*DATA EPROM 104 for the
pedal going down*)
BEGIN
HOLD: = 0; MOTOR: =
FALSE;
FOR I: = TO 511 DO BEGIN
IF I = 511 THEN CODE: =
0 ELSE CODE: = ((I + 1)
DIV 256);
CASE I OF 101:IF
MODES[MODE] <>
'CAUT' THEN HOLD: =
FP2
  218:IF (MODES[MODE]
= 'PHACO') OR (MODES
[MODE]= 'ZERO')
  THEN HOLD: = FP3;
END;
  IF (MODES[MODE]=
'ZERO') AND ((HALF) OR
(FULL)) THEN
CASE I OF 1:MOTOR: =
TRUE;
END;
  IF MODES[MODE] <>
'ZERO' THEN
CASE I OF 55:IF FULL
THEN MOTOR: = TRUE;
```

```
    72:IF (FULL) AND (NOT
HALF) THEN MOTOR: =
FALSE;
    73:IF THEN MOTOR: =
TRUE;
    90:IF MODES[MODE]
<> 'CAUT' THEN
MOTOR: = FALSE;
END;
    IF (MODES)[MODE] =
'PHACO') THEN
CASE I OF 163:IF FULL
THEN MOTOR: = TRUE;
    179:IF (FULL) AND (NOT
HALF) THEN MOTOR: =
FALSE;
    181:IF HALF THEN
MOTOR: = TRUE;
    196:MOTOR: = FALSE;
END;
IF MOTOR THEN CODE:
= CODE + PHASE[I DIV
18 MOD 8] * 16;
CODE: = CODE + HOLD;
IF I > MAXANGLE THEN
CODE: = 1 + OVER;
IF I > 508 THEN CODE: =
1;
WRITELN(DEVICE,'-
.BYTE',CODE:4); END;
CONTROLD; END;
    (*Similar to CONTROL
above, except for the pedal
going down.
    The case statement numbers
are one greater to cause a one
    count dead band, and the
conditional ONUP is not
    included since the pedal is
going down.
    CONTROLU calls
CONTROLD, generating a 1k
page. CONTROLU is
    called twice, with the
conditional ONUP changed
from FALSE
    to TRUE to form a 2k page.
This procedure is called for
    each feedback type and
mode, forming a new 2k file
XXXY.TEXT for
    each combination.*)
PROCEDURE CONTROL;
BEGIN
    IF MODE = 0 AND
(FEEDBACK = 2 OR
FEEDBACK = 3) THEN
EXIT (CONTROL)
    IF MODE = 1 AND
(FEEDBACK = 1 OR
FEEDBACK = 2) THEN
EXIT (CONTROL)
    REWRITE(DEVICE,-
CONCAT(MODES[-
MODE],FEED[FEED-
BACK],'.TEXT'));
    FULL: = BACK
1[FEEDBACK]; (*SET
TRUE OR FALSE FROM
TABLE *)
    HALF: =
BACK[FEEDBACK];
    IF (MODE[MODE]=
ZERO) OR
(MODES[MODE] =
CAUTERY)
    THEN ONUP: = TRUE
ELSE ONUP: = FALSE;
    CONTROLU;
(*GENERAGE CONTROL
CODES")
```

```
    ONUP: = TRUE;
CONTROLU;
(*GENERAGE SET WITH
RETURN FEEDBACK*)
    CLOSE(DEVICE,-
CRUNCH);END; (*END
FEEDBACK LOOP*)
END;
    (*Calls CONTROLU for
the various combinations of the
    conditional ONUP
(feedback when the pedal
returns) and the
    feedback types.*)
BEGIN (*MAIN
PROGRAM*)
    REWRITE(DEVICE,'-
COUNT.TEXT');
    COUNT; (*GENERATE
THE COUNT EPROM*)
    CLOSE(DEVICE,-
CRUNCH);
    INIT; (*SET UP TABLES
FOR MODES*)
    FOR MODE: = 0 TO 4 DO
BEGIN (*FIVE PHACO
PLUS MODES*)
    FOR FEEDBACK: = 0
TO 3 DO BEGIN (*FOUR
FEEDBACK TYPES*)
    CONTROL; END; (*END
FEEDBACK LOOP*)
    REWRITE(DEVICE,-
CONCAT(MODES[-
MODE],'DAC.TEXT'))
    CONVERT; (*BUILD
DAC EPROM FOR EACH
MODE*)
    CLOSE(DEVICE,-
CRUNCH); END; (*END
MODE LOOP*)
END. (*END PROGRAM*)
    (*The main program opens a
disk file COUNT.TEXT and
calls
    COUNT to place the 512
bytes of test into the file.
    There is only one file
required, which must be
assembled
    to generate COUNTER
EPROM 100. It then starts a
dual
    loop, MODE on the outside
and FEEDBACK on the
inside.
    For each MODE there are
four files generated, one for
    each FEEDBACK type,
except for mode ZERO and
mode CAUT
    which only generate two,
since they do not have
plateaus.
    These are excluded by EXIT
statements in the procedure
    CONTROL. Sixteen files
are made, e.g.
PHACO00.TEXT,
    PHACO01.TEXT,etc.)
    After each FEEDBACK
loop a file, e.g.
PHACODAC.TEXT is
    opened, and CONVERT is
called. This generates a file for
    the D/A converter 38, one
for each MODE. Five files can
    be generated.
```

A batch file is needed to combine and assemble the five XXXXDAC.TEXT files to form a 4k code file and DAC EPROM 102.

The DATA files, e.g. PHAC000.TEXT assemble to 2k each and can be concatenated as necessary to form 64k DATA EPROM 104.*)

Although there has been described above a digital electronic foot pedal control system in accordance with the present invention for the purpose of illustrating the manner in which the invention may be used to advantage, it is to be appreciated that the invention is not limited thereto. Accordingly, any and all variations and modifications which may occur to those skilled in the art are to be considered to be within the scope and spirit of the claims appended hereto.

What is claimed is:

1. A digital electronic foot pedal control system for controlling the operation of an associated apparatus, said foot pedal control system comprising:
   a. foot pedal means including a pedal mount, a pedal shaft pivotally mounted to said mount, and a foot-operated pedal fixed to said shaft to pivot therewith;
   b. digital shaft rotational position indicating means connected to said shaft for providing digital shaft position output signals indicative of pedal rotational positions relative to a pedal zero reference position; and
   c. logic means which include:
      (1) digital storage means for storing N given sets of shaft position output control signals which correspond to N given pedal positions, and
      (2) processing means connected for receiving said shaft position output signals from said shaft rotational position indicating means and responsive thereto for causing the outputting from said storage means of corresponding ones of said sets of control signals for controlling the operation of said associated apparatus.

2. The digital electronic foot pedal control system as claimed in claim 1, wherein said digital storage means include an address card having N addresses, each one of said N addresses corresponding to a particular one of said N shaft rotational positions, and each one of said addresses storing a corresponding set of output control signals.

3. The digital electronic foot pedal control system as claimed in claim 2, wherein said processing means include counting means for counting the shaft position output signals from the shaft rotational position indicating means and for deriving therefrom address pointers corresponding to shaft rotational positions for application to said address card.

4. The digital electronic foot pedal control system as claimed in claim 1, wherein the apparatus to be controlled by said foot pedal control system has a plurality of operating functions and means for selecting among said functions, and wherein said digital storage means include a plurality of address cards, each of said address cards corresponding to one or more of said functions and being selected in response to said selecting means selecting among said functions, each of said address cards having N address, each one of which corresponds to a particular one of said N shaft rotational positions, and each one of said N addresses storing a set of output control signals for the corresponding pedal shaft position.

5. The digital electronic foot pedal control system as claimed in claim 4, wherein said processing means include counting means for counting the shaft position output signals from the shaft rotational position indicating means and for deriving therefrom address pointers which correspond to pedal shaft positions, and further including means responsive to said means for selecting among said functions for causing said address pointers to be applied to the address card which corresponds to the selected function or functions.

6. The digital electronic foot pedal control system as claimed in claim 1, including motor means connected to said shaft so as to drive said shaft in a rotational direction back toward said zero reference position when the pedal is displaced therefrom and when said motor means are energized, said motor means thereby providing a resistance to, but not preventing, further pedal rotational movement away from said zero reference position.

7. The digital electronic foot pedal control system as claimed in claim 6, wherein given sets of output control signals stored in said digital storage means include control signals for causing the energizing of said motor means at given pedal rotational positions.

8. The digital electronic foot pedal control system as claimed in claim 6, wherein said motor means comprise a stepper motor.

9. A digital electronic foot pedal control system for controlling the operation of an associated apparatus, said foot pedal control system comprising:
   a. foot pedal means including a pedal mount, a pedal shaft pivotally mounted to said mount, and a foot-operated pedal fixed to said shaft to pivot therewith;
   b. digital shaft rotational position indicating means connected to said shaft for providing digital shaft position output signals indicative of pedal angular position relative to a pedal zero reference position; and
   c. logic means which include:
      (1) digital storage means for storing N given sets of output control signals which correspond to N given pedal angular positions relative to said reference position, said digital storage means including one or more address cards each having N addresses, each one of said addresses corresponding to one of said N given shaft rotational positions and storing corresponding sets of given control output signals for controlling the operation of said associated apparatus; and
      (2) processing means connected for receiving said shaft position output signal from said shaft rotational position indicating means and including counting means for counting the shaft position output signals from the shaft rotational position indicating means and for deriving therefrom shaft position address pointers for applying to said one or more address cards to thereby cause the outputting therefrom of said sets of given control signals.

10. The digital electronic foot pedal control system as claimed in claim 9, wherein the apparatus to be controlled by said foot pedal control system has a plurality of operating functions and means for selecting among said functions, and including a plurality of said address cards, wherein each of said digital storage address cards corresponds to one or more of said functions, and said address cards being selected in response to said selecting means selecting among said functions.

11. The digital electronic foot pedal control system as claimed in claim 9, including a stepper motor connected to said pedal shaft for the driving thereof in a rotational direction toward said zero reference position when the pedal is displaced therefrom and when said stepper motor is energized, said stepper motor thereby providing a resistance to, but not preventing, further pedal shaft rotational movement away from said zero reference position.

12. The digital electronic foot pedal control system as claimed in claim 11, wherein given sets of output control signals stored in said digital storage means include control signals for causing the energizing of said stepper motor at given pedal rotational positions.

13. A digital electronic foot pedal control system for controlling the operation of an associated apparatus, said foot pedal control system comprising:
 a. foot pedal means including a pedal mount, a pedal shaft pivotally mounted to said mount, and a foot-operated pedal fixed to said shaft to pivot therewith;
 b. digital shaft rotational position indicating means connected to said shaft for providing digital shaft position output signals indicative of pedal angular position relative to a pedal zero reference position;
 c. logic means which include:
   (1) digital storage means for storing N given sets of output control signals which correspond to N given pedal shaft angular positions relative to said reference position, said digital storage means including one or more address cards each having N addresses, each one of said N addresses corresponding to one of said N shaft rotational positions and storing corresponding sets of given control output signals for controlling the operation of said associated apparatus; and
   (2) processing means connected for receiving said shaft position output signal from said shaft rotational position indicating means and including counting means for counting the shaft position output signals from the shaft rotational position indicating means and for deriving therefrom appropriate address pointers for applying to said one or more address cards to thereby cause the outputting therefrom of said sets of control signals corresponding to pedal shaft positions; and
 d. motor means connected to said shaft for driving said shaft in a rotational direction toward said zero reference position when the pedal is displaced therefrom and when said motor means are energized, said motor means thereby providing a resistance to, but not preventing, further pedal rotational movement away from said zero reference position.

14. The digital electronic foot pedal control system as claimed in claim 13, wherein given ones of said sets of output control signals stored in said digital storage means include control signals for causing the energizing of said motor means at given pedal rotational positions.

15. The digital electronic foot pedal control system as claimed in claim 13, wherein said motor means comprise a stepper motor.

16. The digital electronic foot pedal control system as claimed in claim 13, wherein the apparatus to be controlled by said foot pedal control system has a plurality of operating functions and means for selecting among said functions, and including a plurality of said address cards, wherein each of said digital storage address cards corresponds to one or more of said functions, said address cards being selected in response to said selecting means selecting among said functions.

17. A digital electronic foot pedal control system for controlling the operation of an associated apparatus, said foot pedal control system comprising:
 a. foot pedal means including a pedal mount, a pedal shaft pivotally mounted to said mount, and a foot-operated pedal fixed to said shaft to pivot therewith;
 b. digital shaft rotational position indicating means connected to said shaft for providing a digital shaft position output signal indicative of pedal angular position relative to a pedal zero reference position;
 c. logic means which include:
   (1) digital storage means for storing N given sets of output control signals which correspond to N given pedal angular positions relative to said reference position, and
   (2) processing means connected for receiving said shaft position output signal from said shaft rotational position indicating means and responsive thereto for causing the outputting from said storage means of corresponding sets of control signals for controlling the operation of said associated apparatus, said control signals corresponding to shaft rotational positions indicated by said received shaft position output signal; and
 d. motor means connected to said pedal shaft so as to drive said pedal shaft in a rotational direction toward said zero reference position when the pedal shaft is displaced therefrom and when said motor means are energized, said motor means thereby providing a resistance, but not preventing, further pedal shaft rotational movement away from said zero reference position.

18. The digital electronic foot pedal control system as claimed in claim 17, wherein given ones of said sets of output control signals stored in said digital storage means include control signals for causing the energizing of said motor means at given pedal shaft rotational positions.

19. The digital electronic foot pedal control system as claimed in claim 17, wherein said motor means comprise a stepper motor.

20. The digital electronic foot pedal control system as claimed in claim 17, wherein said processing means include counting means for counting the shaft position output signals from the shaft rotational position indicating means and for deriving therefrom address pointers for application to said address card.

21. The digital electronic foot pedal control system as claimed in claim 17, wherein the apparatus to be controlled by said foot pedal control system has a plurality of operating functions and means for selecting among said functions, and wherein said digital storage means include a plurality of address cards, each of said address cards corresponding to one or more of said functions and being selected in response to said selecting means selecting among said functions.

22. The digital electronic foot pedal control system as claimed in claim 21, wherein said processing means include counting means for counting the shaft position output signals from the shaft rotational position indicating means and for driving address pointers therefrom and further including means responsive to said means for selecting among said functions for applying said address pointers to the address card which corresponds to the selected function.

23. A digital electronic foot pedal control system, especially useful for medical apparatus having a plurality of operating functions and means for selecting among said functions, said foot pedal control system comprising:
   a. foot pedal means including a pedal mount, a pedal shaft pivotally mounted to said mount, and a foot-operated pedal fixed to said shaft to pivot therewith;
   b. digital shaft rotational position indicating means connected to said shaft for providing a digital shaft position output signal indicative of pedal angle relative to a pedal zero reference position;
   c. logic means which include:
      (1) digital storage means for storing N given sets of output control signals which correspond to N given pedal shaft angular positions relative to said reference position, said digital storage means including a plurality of address cards each having N addresses, each of said address cards corresponding to one or more of said functions and being selected in response to said selecting means selecting among said function, and each of said N addresses corresponding to a particular one of said N shaft rotational positions and storing a corresponding set of control output signals for operating said medical apparatus; and
      (2) processing means connected for receiving said shaft position output signal from said shaft rotational position indicating means and including counting means for counting the shaft position output signals from the shaft rotational position indicting means and for deriving address pointers therefrom, and further including means responsive to said means for selecting among said functions for applying said address pointers to the address card which corresponds to the selected function to thereby cause the outputting therefrom of appropriate ones of said sets of given control signals; and
   d. a stepper motor connected to said pedal shaft for driving said shaft in a rotational direction toward said zero reference position when the shaft is displaced therefrom and when said stepper motor is energized, said stepper motor thereby providing a resistance to, but not preventing, further pedal rotational movement away from said zero reference position, given ones of said sets of output control signals stored in said digital storage means including control signals for causing the energizing of said stepper motor at given pedal rotational positions.

24. The digital electronic foot pedal control apparatus as claimed in claim 1, wherein the logic means include means for providing an analog output signal proportional to said pedal shaft position.

25. The digital electronic foot pedal control apparatus as claimed in claim 9, wherein the logic means include means for providing an analog output signal proportional to said pedal shaft position.

* * * * *